United States Patent [19]

Allman et al.

[11] Patent Number: 5,184,015
[45] Date of Patent: Feb. 2, 1993

[54] CHARGED PARTICLE MOBILITY REFRIGERANT ANALYZER

[75] Inventors: Steve L. Allman; Chung-Hsuan Chen; Fang C. Chen, all of Knoxville, Tenn.

[73] Assignee: Martin Marietta Energy Systems, Inc., Oak Ridge, Tenn.

[21] Appl. No.: 766,542

[22] Filed: Sep. 27, 1991

[51] Int. Cl.$^5$ .................. B01D 59/44; H01J 49/00
[52] U.S. Cl. .................... 250/282; 250/286; 250/287
[58] Field of Search ............ 250/281, 282, 283, 288, 250/286, 287, 423 P

[56] References Cited

U.S. PATENT DOCUMENTS

| | | | |
|---|---|---|---|
| 2,950,387 | 8/1960 | Brubaker | 250/423 P |
| 3,211,996 | 10/1965 | Fox et al. | |
| 3,621,239 | 11/1971 | Cohen | |
| 3,626,180 | 12/1971 | Carroll | |
| 3,639,756 | 2/1972 | Schulz | |
| 3,697,748 | 10/1972 | Cohen | |
| 3,699,333 | 10/1972 | Cohen et al. | |
| 3,742,213 | 6/1973 | Cohen et al. | |
| 4,007,624 | 2/1977 | Chantry et al. | |
| 4,378,499 | 3/1983 | Spangler et al. | 250/281 |
| 4,574,004 | 3/1986 | Schmidt-Ott | |
| 4,769,548 | 9/1988 | Burtscher et al. | |
| 4,772,794 | 10/1988 | Jenkins | 250/288 |
| 4,777,363 | 10/1988 | Eiceman et al. | 250/286 |
| 4,950,893 | 8/1990 | Reategui | 250/287 |

*Primary Examiner*—Bruce C. Anderson
*Attorney, Agent, or Firm*—Joseph A. Marasco; Harold W. Adams

[57] ABSTRACT

A method for analyzing a gaseous electronegative species comprises the steps of providing an analysis chamber; providing an electric field of known potential within the analysis chamber; admitting into the analysis chamber a gaseous sample containing the gaseous electronegative species; providing a pulse of free electrons within the electric field so that the pulse of free electrons interacts with the gaseous electronegative species so that a swarm of electrically charged particles is produced within the electric field; and, measuring the mobility of the electrically charged particles within the electric field.

5 Claims, 2 Drawing Sheets

CHARGED PARTICLE MOBILITY REFRIGERANT ANALYZER

The U.S. Government has rights in this invention pursuant to contract no. DE-AC05-84OR21400 between the U.S. Department of Energy and Martin Marietta Energy Systems, Inc.

FIELD OF THE INVENTION

The present invention relates to methods and apparatus for detecting and analyzing small quantities of electronegative species. More particularly, the invention relates to such methods and apparatus which measure charged particle mobility.

BACKGROUND OF THE INVENTION

Chlorofluorocarbon (CFC) heat exchanging compositions, referred to hereinafter as refrigerants, currently used in heat pumps, air conditioners, and refrigerators, are now known to have serious environmental effects due to destructive reactions with ozone in the Earth's atmosphere. It is believed that the chlorine atom in these refrigerants is the "culprit" which leads to the destruction of the ozone layer. Thus, refrigerant containing any chlorine atom as part of its chemical composition will likely be prohibited for use in air conditioners. Non-CFC refrigerants which have no Cl atom in their chemical structure, such as fluorocarbons, will likely be used to replace CFC refrigerants currently in use.

However, until suitable lubricants are developed, the transition to non-CFC refrigerants is expected to be gradual. During the transition period, refrigerant mixtures containing some percentage of CFC will likely be used. The presence of CFC will provide for circulation of presently used lubricants, which do not circulate well when used with pure non-CFC refrigerants. The nature, or makeup, of these mixtures can vary widely. Furthermore, mixtures of refrigerants may be found to be suitable for permanent use.

Hence, it is necessary, especially when servicing a refrigeration unit, to analyze the refrigerant to determine if a pure refrigerant or a mixture is present in the system. It is also necessary to determine the nature of the mixture, if a mixture is present. There is a need for methods and apparatus for identifying and determining the relative quantities of component species in those mixtures. What is needed is a relatively simple means for connecting into a refrigeration system and determine what types of refrigerants are being used in the system. This is particularly useful when mixtures of chlorinated and non-chlorinated refrigerants are required in refrigeration systems in support of efforts to protect the Earth's atmospheric ozone layer. For example, in order to re-charge a refrigeration system or air conditioner, it would be first necessary to verify what mix of refrigerants is already in the system. As legislation is passed setting limits on the fraction of chlorinated refrigerants allowed in mixtures, the further usefulness of such methods and apparatus in law compliance and enforcement efforts is evident.

OBJECTS OF THE INVENTION

Accordingly, it is an object of the present invention to provide new and improved methods for protecting the environment.

It is another object of the invention to provide a new and improved method and apparatus for detecting and analyzing refrigerants.

It is a further object of the invention to provide a new and improved method and apparatus for detecting and analyzing electronegative species.

It is also an object of the invention to provide methods and apparatus for analyzing mixtures of electronegative species to identify and determine the relative quantities of component species in such mixtures.

Further and other objects of the present invention will become apparent from the description contained herein.

SUMMARY OF THE INVENTION

In accordance with one aspect of the present invention, the foregoing and other objects are achieved by a method for analyzing a gaseous electronegative species comprises the steps of providing an analysis chamber; providing an electric field of known potential within the analysis chamber; admitting into the analysis chamber a gaseous sample containing the gaseous electronegative species; providing a pulse of free electrons within the electric field so that the pulse of free electrons interacts with the gaseous electronegative species so that a swarm of electrically charged particles is produced within the electric field; and, measuring the mobility of the electrically charged particles within the electric field.

For a better understanding of the present invention, together with other and further objects, advantages and capabilities thereof, reference is made to the following disclosure and appended claims in connection with the above-described drawing.

DETAILED DESCRIPTION OF THE INVENTION

Many refrigerants have halogen atoms as part of their chemical compositions. Since compounds containing halogen tend to attract electrons to form negative ions, detection of these negative ions forms a basis for detecting the presence of refrigerants and other electronegative species. Hence, exposing a gaseous sample to a source of electrons followed by measuring drift velocity of the negative charge can be used to detect the presence of electronegative species, and analyze the nature thereof.

The present invention finds basis in measurements based upon two different approaches which are a result of phenomena occurring within the apparatus described herein: (1) the production of parent ions and measurement of these parent ions based on their mobilities; and (2) the measurement of collection time of charged particles, primarily electrons.

The first approach is based on ion mobilities exhibited by different molecules. If only parent ions of refrigerants are produced, different kinds of refrigerant can be distinguished from their different mobility coefficients. However, some refrigerants, such as R12, are well known to dissociate to form halogen ions after relatively high energy electrons are captured. In order to sustain a parent ion intact, the electrons should be produced at very low energy, for instance, 0.5 ev or less. This approach can also be applied to leak detection.

The second approach is to measure collection time of charged particles for refrigerant mixtures. Electron drift velocity is determined by the media and is characteristic of the media. Thus, the percentage of each refrigerant in refrigerant mixtures can be determined. This approach is useful for determining the nature of refrigerant mixtures.

Figure 1:
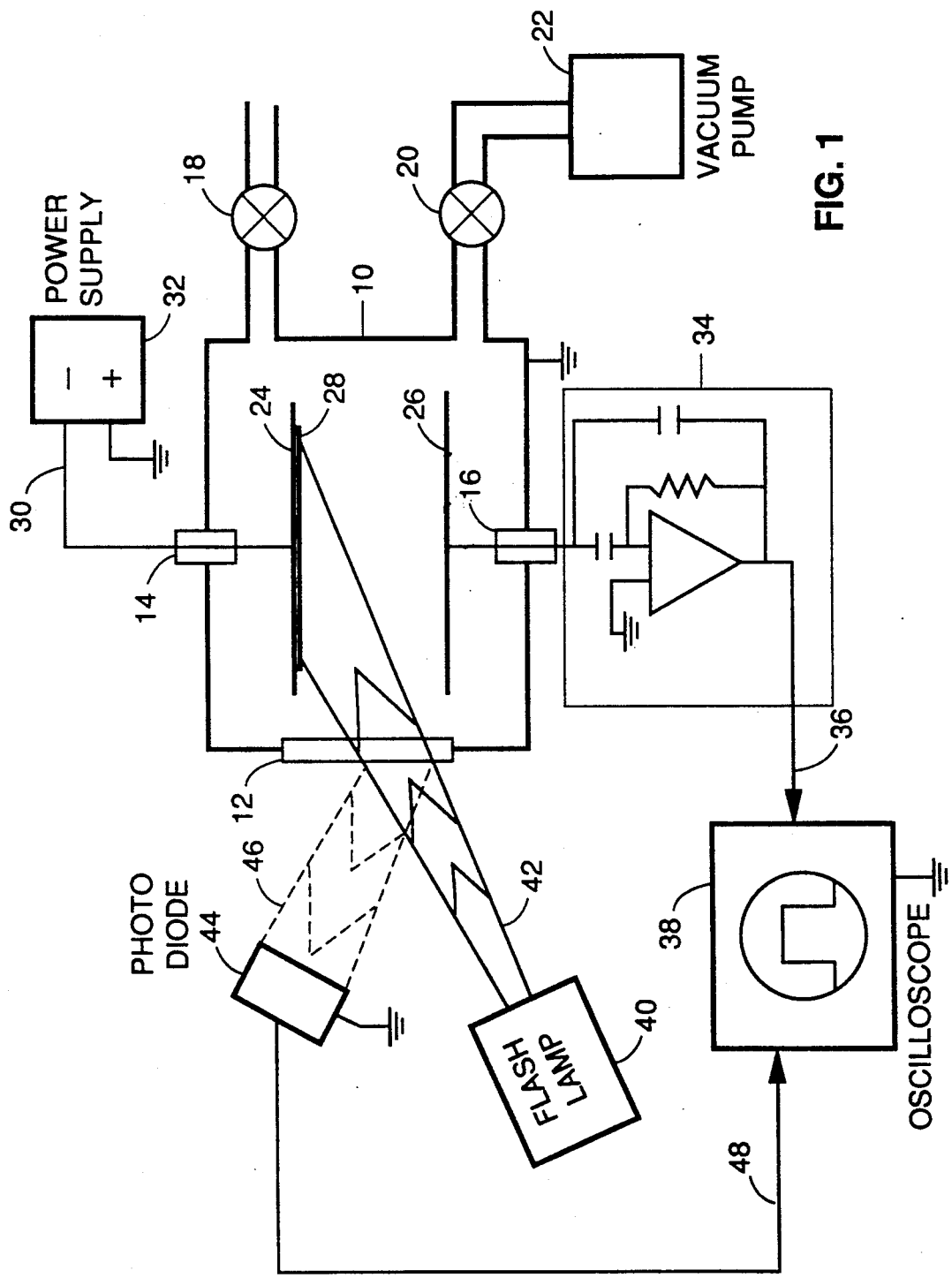
FIG. 1 is a schematic view of an apparatus for carrying out the subject invention.

Referring now to FIG. 1, an apparatus in accordance with the invention may be described as follows. A stainless steel vacuum chamber 10 is equipped with a quartz window 12, electrical feedthroughs 14, 16, and a valved sample inlet 18. Valved outlet 20 may optionally be a pressure relief valve or can be connected to a vacuum pump 22, depending on the desired operating pressures. A versatile option would be to have both pressure and vacuum available. The electrical feedthroughs 14, 16 are connected to parallel stainless steel plate electrodes 24, 26 positioned inside the chamber 10 so that radiant energy can be directed through the window 12 onto the first electrode 24. The first electrode 24 is an emitter electrode and is overlaid with a plate 28 comprised of cesium/antimony alloy or other low work function metal, which is known to emit photo-electrons when illuminated by ultraviolet light. The first electrode 24 is connected through feedthrough 14 to the negative output 30 of a direct current power supply 32. The second electrode 26 is a collector electrode, and is connected through feedthrough 16 through a charge sensitive preamplifier 34 to the signal input 36 of an oscilloscope 38. A suitable preamplifier 34 typically has a fast rise time and slow decay, and is capable of amplifying the electron current between the electrodes 24, 26 sufficiently to observe indicative signals on the oscilloscope 38. The gain of a typically suitable preamplifier 34 is such that the movement of approximately 300,000 electrons from the first stainless steel plate to the second results in a voltage pulse out of the preamplifier of approximately 50 millivolts. In the course of operating the device, signals observed from the preamplifier 34 could range in amplitude from less than 1 millivolt to several hundred millivolts.

A pulsing flashlamp 40, or another source of radiant energy, is positioned so that a beam of radiant energy 42 emitted therefrom is directed through the quartz window 12 at onto the plate 28.

A photodiode 44, or other appropriate detector, is positioned to receive at least part of the portion of radiant energy beam 42 that is reflected from the quartz window 12. An optical waveguide, not illustrated, could also be used to capture a portion of the radiant energy beam 42 and transfer it to the photodiode 44. The output of the photodiode 44 is connected to the trigger input 48 of the oscilloscope 38. The oscilloscope 38 can also be triggered by an electrical signal generated by the flashlamp 40. If a waveform digitizer type oscilloscope 38 is used, it can be set to generate a trigger signal derived from the voltage amplitude of the waveform being sampled, eliminating the need for a separate trigger signal.

Another option, not requiring the use of a low work function metal plate 28, is to dispose a collimated nuclear radiation source so that a radioactive beam is directed between the electrodes 24, 26, and parallel to the positive electrode 26. The radioactive beam will ionize particles in a line parallel to electrode 26 to initiate the analysis process.

To operate the apparatus, a gaseous sample is introduced into the analysis chamber 10 through the inlet valve 18, and a suitable pressure is maintained therein. The actual pressure is not as significant as is the maintenance of a constant pressure.

An electrical potential is applied to the first electrode 24 through a vacuum tight ceramic insulated electrical feedthrough from the DC power supply 32. The most suitable electrical potential is dependent upon sample quantity (pressure) and composition and electrode spacing; a suggested value would be about negative 2500 volts at a pressure of one atmosphere for electrodes spaced about 2 cm apart. A pulse of ultraviolet light (UV), produced by the flashlamp 40, is directed through the quartz window 12 and onto the cesium/antimony alloy plate 28. A pulse of photoelectrons is ejected from the plate 28, and is attracted to the positive electrode 26. The photoelectrons continuously interact with sample molecules between the electrodes 24, 26. These interactions produce the measurable phenomenon from which useful data is generated.

The interactions are monitored through the preamplifier circuit 34 by the signal input 36 of the oscilloscope 38. If a trigger circuit is used as shown in FIG. 1, the photodiode 44 receives the portion of UV beam 42 that is reflected from the quartz window 12 and activates the trigger input 48 of the oscilloscope 38. Data relating to ion mobility and collection time can be read directly from the oscilloscope 38.

EXAMPLE I

Figure 2:
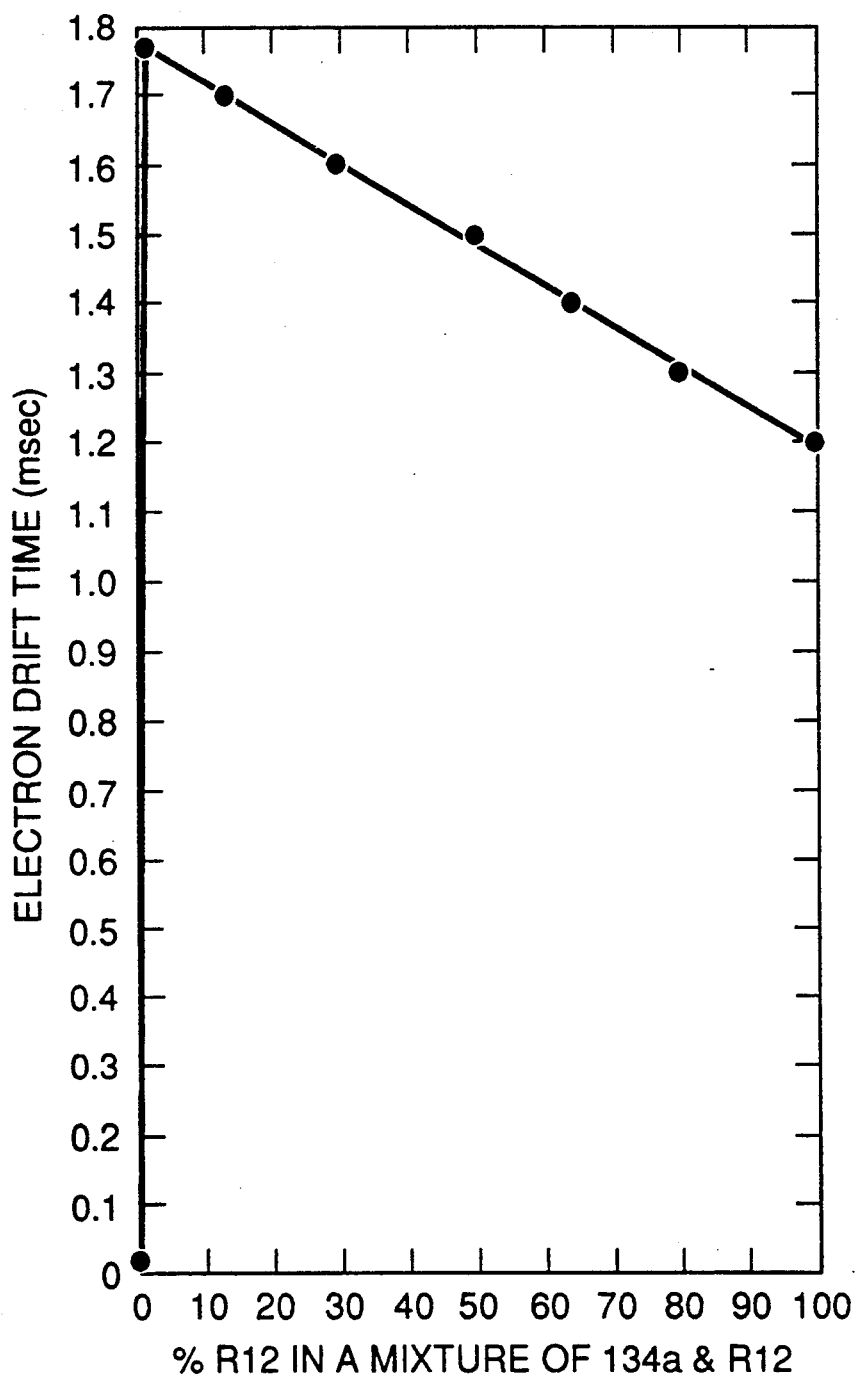
FIG. 2 is a graph representing data collected during a test of the subject invention.

Measurements were made of binary mixtures which include R134A and R12 in different ratios. Charged particle drift times were determined by comparing the full-width of observed peaks at half-magnitude. FIG. 2, shows drift time versus the percentage of R12 in R12 and R134A binary mixtures. The first data point indicates that the charged particles in pure R134A are highly mobile, and are collected very quickly, implying that slow electrons are not easily attached to R134A. However, when a small amount of R12 is added, most of the free electrons were attached to R12. The second data point is for 0.5% R12, and indicates drastically decreased drift velocity. However, as more R12 was added, the drift velocity for charged particles increased gradually, producing a calibrated curve which is useful for determining the makeup of a mixture of the two refrigerants.

EXAMPLE II

Mixtures of R152A and R134A were tested in the same manner as shown above. Similar phenomena were observed, indicating that the same method can be used to determine the ratio of concentrations of R152A and R134A.

EXAMPLE III

Mixtures of R152A and R12 are tested in the same manner as shown above. Similar phenomena are observed, indicating that the same method can be used to determine the ratio of concentrations of R152A and R12.

EXAMPLE IV

Mixtures of refrigerants and air were tested in the same manner as shown above. The observation was that the collection time for charged particles is much longer for a mixture of R12, R134A and air, compared to a mixture of R134A and air, indicating that the same method can be used to analyze mixtures of refrigerants in air.

EXAMPLE V

An automobile air conditioner, charged with a mixture of refrigerants, becomes inoperative due to a refrigerant leak. A sample of refrigerant remaining in the air conditioner is drawn into the above described apparatus. The above described method is used to determine the percentage of each refrigerant. The air conditioner is then recharged to the correct concentration of each refrigerant.

EXAMPLE VI

An automobile air conditioner is to be tested for compliance to regulations regarding the nature of the refrigerant contained therein. A sample of refrigerant is drawn from the air conditioner into the above described apparatus. The above described method is used to determine the nature of the refrigerant.

While there has been shown and described what are at present considered the preferred embodiments of the invention, it will be obvious to those skilled in the art that various changes and modifications can be made therein without departing from the scope of the inventions defined by the appended claims.

What is claimed is:

1. A method for determining the makeup of a mixture of known refrigerants comprising the steps of:
    providing an analysis chamber;
    providing an electric field of known potential within said analysis chamber;
    admitting into said analysis chamber a gaseous sample containing a mixture of known refrigerants;
    providing a pulse of free electrons within said electric field so that said pulse of free electrons interacts with said mixture so that a swarm of electrically charged particles is produced within said electric field;
    measuring the mobility of said electrically charged particles within said electric field; and,
    comparing said measurement to data obtained from mixtures of said refrigerants having known makeup.

2. The method as defined in claim 1 wherein said electric field is provided by a circuit means comprising a pair of spaced electrodes, one electrode being negatively charged with respect to the other electrode.

3. The apparatus as defined in claim 2 wherein said pulse of free electrons is provided by a pulsing means comprising a low work function metal surface on said negatively charged electrode, said low work function metal surface facing said other electrode; and an illuminating means for illuminating said low work function metal surface with ultraviolet light.

4. The method as defined in claim 1 wherein said pulse of free electrons is provided by a radioactive source disposed to provide a collimated beam of radiation within said electric field.

5. The method as defined in claim 1 further comprising a step for controlling gas pressure within said analysis chamber.

* * * * *